(12) United States Patent
Carmi (10) Patent No.: US 9,478,024 B2
(45) Date of Patent: Oct. 25, 2016

(54) PERFUSION IMAGING (71) Applicant: KONINKLIJKE PHILIPS N.V., Eindhoven (NL)

(72) Inventor: Raz Carmi, Haifa (IL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 15 days.

(21) Appl. No.: 14/436,492

(22) PCT Filed: Oct. 31, 2013

(86) PCT No.: PCT/IB2013/059829
§ 371 (c)(1),
(2) Date: Apr. 17, 2015

(87) PCT Pub. No.: WO2014/068520
PCT Pub. Date: May 8, 2014

(65) Prior Publication Data
US 2016/0048955 A1   Feb. 18, 2016

Related U.S. Application Data (60) Provisional application No. 61/720,475, filed on Oct. 31, 2012.

(51) Int. Cl.
*G06T 7/00* (2006.01)
*G06T 5/40* (2006.01)
(Continued)

(52) U.S. Cl.
CPC .............. *G06T 7/0012* (2013.01); *A61B 6/032* (2013.01); *A61B 6/504* (2013.01); *G06T 5/40* (2013.01);
(Continued)

(58) Field of Classification Search
CPC ..... G06T 5/40; G06T 7/0012; G06T 7/0081; G06T 15/08; G06T 2200/04; G06T 2207/10076; G06T 2207/10081; G06T 2207/30024; G06T 2207/30061; G06T 2207/30101; G06T 2210/41; G06T 2211/40; A61B 6/032; A61B 6/504
See application file for complete search history.

(56) References Cited

U.S. PATENT DOCUMENTS

2003/0211036 A1   11/2003   Degani et al.
2004/0218794 A1   11/2004   Kao et al.
(Continued)

FOREIGN PATENT DOCUMENTS

WO   2008114016 A2   9/2008
WO   2011001332 A1   1/2011

OTHER PUBLICATIONS

Bernstine et al., "FDG PET/CT Early Dynamic Blood Flow and Late Standardized Uptake Value Determination in Hepatocellular Carcinoma", Aug. 2011, Radiology, vol. 260, Iss 2, 503-510.*
(Continued)

*Primary Examiner* — Katrina Fujita (57) ABSTRACT

Described herein is an approach for analyzing perfusion characteristics of heterogeneous tissues in 4D data set (i.e., a time series of contrast enhanced 3D volumes) in which spatially entangled tissue components are separated into individual tissue components and perfusion maps for the individual tissue components are generated and visually presented. In one instance, the approach includes obtaining the 4D data set in electronic format, generating a different time activity curve point for each of the different tissue components for each voxel being evaluated for each time frame being evaluated, and generating a signal indicative of a different parameter map for each of the different tissue components based at least on the time activity curves. Optionally, relations between parameters of the different components are determined and presented in relation maps.

20 Claims, 12 Drawing Sheets

(51) Int. Cl.
*A61B 6/03* (2006.01)
*A61B 6/00* (2006.01)
*G06T 15/08* (2011.01)

(52) U.S. Cl.
CPC ............. *G06T 7/0081* (2013.01); *G06T 15/08* (2013.01); *G06T 2200/04* (2013.01); *G06T 2207/10076* (2013.01); *G06T 2207/10081* (2013.01); *G06T 2207/30024* (2013.01); *G06T 2207/30061* (2013.01); *G06T 2207/30101* (2013.01); *G06T 2210/41* (2013.01); *G06T 2211/40* (2013.01)

(56) References Cited

U.S. PATENT DOCUMENTS

| | | |
|---|---|---|
| 2008/0221441 A1 | 9/2008 | Bjornerud et al. |
| 2008/0230703 A1* | 9/2008 | Kadrmas ............... G01T 1/1611 250/363.03 |
| 2008/0262344 A1 | 10/2008 | Brummett |
| 2012/0197117 A1 | 8/2012 | Picot et al. |
| 2014/0254909 A1* | 9/2014 | Carmi ................... A61B 6/032 382/131 |
| 2015/0080707 A1* | 3/2015 | Carmi ................... A61B 8/06 600/415 |

OTHER PUBLICATIONS

Chen, L., et al.; CAM-CM: a signal deconvolution tool for in vivo dynamic contrast-enhanced imaging of complex tissues; 2011; Bioinformatics; 27(18)2607-2609.

Chou, Y-C., et al.; Classification of hemodynamics from dynamic-susceptibility-contrast magnetic resonance (DSC-MR) brain images using noiseless independent factor analysis; 2007; Medical Image Analysis; 11:242-253.

DiNallo, A. M., et al.; Quantitative analysis of CT-perfusion parameters in the evaluation of brain gliomas and metastases; 2009; Journal of Experimental & Clinical Cancer Research; 28:38-47.

Fenchel, M., et al.; Perfusion MR Imaging with FAIR True FISP Spin Labeling in Patients with and without Renal Artery Stenosis: Initial Experience; 2006; Radiology; 238(3)1013-1021.

Mehrabian, H., et al.; A constrained independent component analysis technique for artery-vein separation of two-photon laser scanning microscopy images of the cerebral microvasculature; 2012; Medical Image Analysis; 16:239-251.

* cited by examiner

PERFUSION IMAGING

CROSS REFERENCE TO RELATED APPLICATIONS

This application is a national filing of PCT application Serial No. PCT/IB2013/059829, filed Oct. 31, 2013, published as WO 2014/068520 A1 on May 8, 2014, which claims the benefit of U.S. provisional application Ser. No. 61/720,475 filed Oct. 31, 2012, which is incorporated herein by reference.

The following generally relates to perfusion imaging and is described with particular application to computed tomography (CT); however, the following is also amenable to other imaging modalities including magnetic resonance imaging (MRI), positron emission tomography (PET), single photon emission computed tomography (SPECT), ultrasound (US) and/or other imaging modalities.

CT perfusion imaging provides functional information through imaging characteristics related to the blood flow in organs and tissues using a contrast material such as iodine contrast agent. A typical perfusion study requires repeated imaging of the volume of interest for a number of different time points, for example, 3-30 repeated scans with a few seconds difference between successive scans (e.g. 1 to 10 sec per time frame). In common perfusion techniques, a bolus of a contrast agent is administered into the patient's vascular system and images from the region of interest are collected for a period covering the transit of the contrast agent bolus through the tissue in the region of interest.

The local concentration changes of the contrast agent over time are used for analyzing physiological parameters. In clinical practice, it is common for the perfusion image series to be inspected qualitatively or to be assessed quantitatively with special analysis algorithms. A quantified result may include, for a region or per voxel, a measurement of blood flow, blood volume, mean transit time, time of arrival, permeability, time to peak, peak intensity, maximal gradient, and/or other parameters. Perfusion imaging of heterogeneous tissues, which is relevant to many tumor types and/or other tissue, often poses challenges for accurate perfusion quantification.

By way of example, different tissue components can be spatially entangled within a region of interest and, thus, even subtle patient or organ motion during the dynamic acquisition can introduce significant analysis errors as the time series may not be spatially-aligned. One approach to reduce this has been to smooth the images and to calculate average perfusion values of the organ regions. Another approach to reduce this has been to analyze, collectively, the voxels in a region of interest, e.g., by using histogram or segmentation techniques. Unfortunately, such approaches still do not provide comprehensive analysis of perfusion parameters of heterogeneous tissues.

Aspects described herein address the above-referenced problems and others.

The following describes an approach for analyzing perfusion characteristics of spatially entangled heterogeneous tissues in 4D image data (i.e., a time series of contrast enhanced 3D volumes) in which spatially entangled tissue components are separated and perfusion maps for the individual tissue components are generated and visually presented.

In one aspect, a method includes obtaining a 4D data set in electronic format, wherein the 4D data set includes a plurality of 3D volumes of voxels of contrast enhanced perfusion imaging data for two or more time frames, and the 3D volumes include data representative of at least two different tissue components in a same region of interest in at least one of the time frames, generating a different time activity curve point for each of the different tissue components for each voxel being evaluated for each time frame being evaluated, and generating a signal indicative of a different parameter map for each of the different tissue components based at least on the time activity curves.

In another aspect, a processing system includes a histogram generator that generates a histogram for each voxel being evaluated in a plurality of 3D volumes of voxels of contrast enhanced perfusion imaging data for two or more time frames, wherein the 3D volumes include data representative of at least two different tissue components in a same region of interest in at least one of the time frames, a time activity curve (TAC) generator that generates a different time activity curve point for each of the different tissue components for each voxel being evaluated for each time frame being evaluated, and perfusion map generator that generates a signal indicative of a different parameter map for each of the different tissue components based at least on the time activity curves.

In another aspect, an imaging system includes a computer readable storage medium encoded with one or more computer executable instructions, which, when executed by a processor of a computing system, causes the processor to: analyze perfusion characteristics of heterogeneous tissue by separating spatially entangled tissue components into two or more tissue classes and generating a set of perfusion maps for each of the individual tissue components.

The invention may take form in various components and arrangements of components, and in various steps and arrangements of steps. The drawings are only for purposes of illustrating the preferred embodiments and are not to be construed as limiting the invention.

The following describes an approach for analyzing perfusion characteristics of spatially entangled heterogeneous tissues in 4D image data in which spatially entangled tissue components are separated and perfusion maps for the individual tissue components are generated and visually presented.

Figure 1:
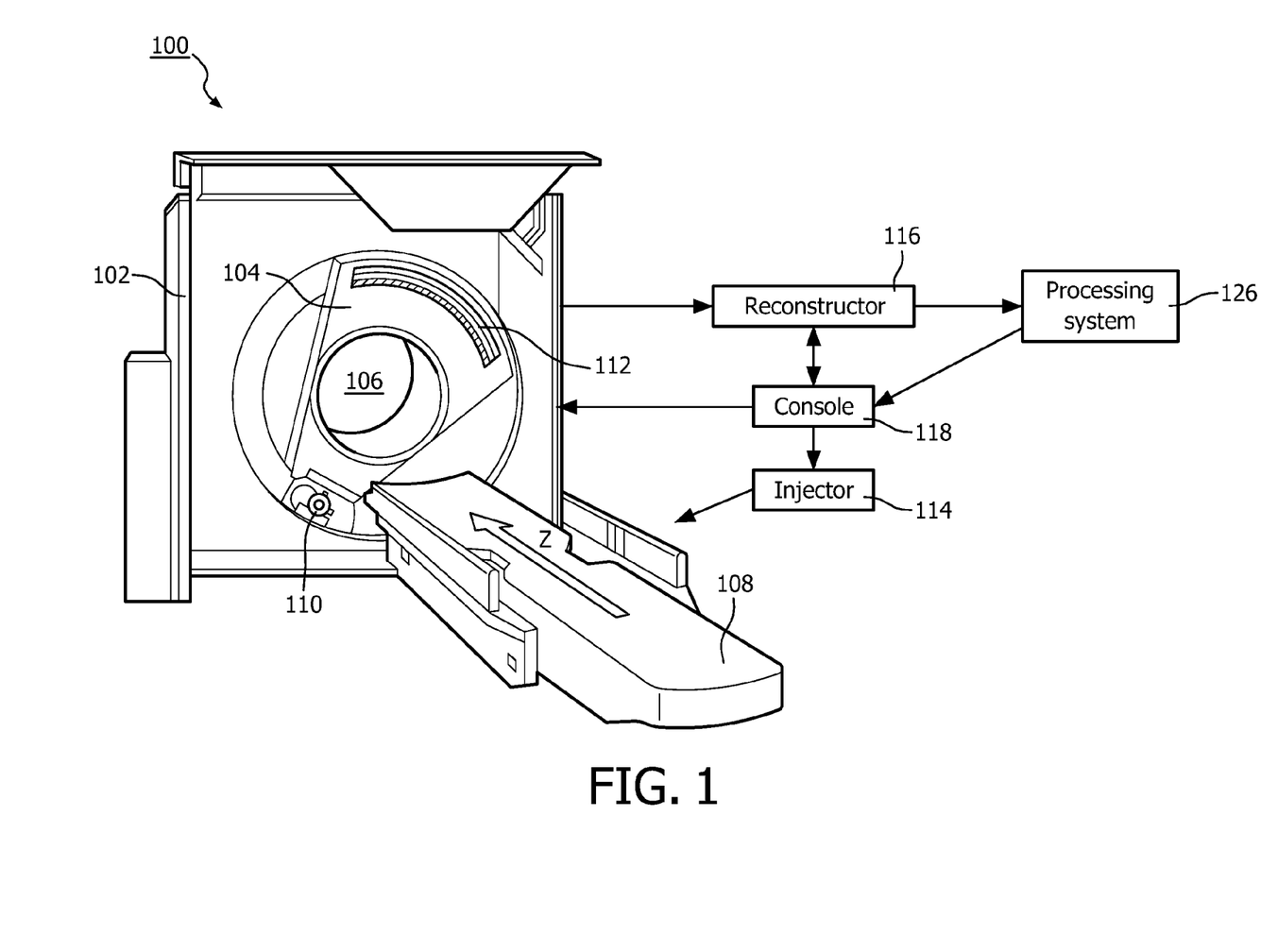
FIG. 1 schematically illustrates an example processing system in connection with an imaging system.

FIG. 1 schematically illustrates an example imaging system 100 such as a CT scanner. In other embodiments, the imaging system 100 can include one or more of an MRI, PET, SPECT, US, a combination thereof, and/or other imaging system configured to perform dynamic contrast enhanced imaging scans. The illustrated imaging system 100 includes a stationary gantry 102 and a rotating gantry 104, which is rotatably supported by the stationary gantry 102 and rotates around an examination region 106 about a z-axis.

A radiation source 110, such as an x-ray tube, is rotatably supported by the rotating gantry 104, rotates with the rotating gantry 104, and emits polychromatic radiation that traverses the examination region 106. A radiation sensitive detector array 112 subtends an angular arc opposite the radiation source 110 across the examination region 106, detects radiation traversing the examination region 106, and generates a signal indicative thereof. A subject support 108 supports an object or subject in the examination region 106.

An optional injector 114 is configured to inject a contrast material(s), for example, for a contrast enhanced imaging procedure, such as a perfusion scan. The illustrated injector 114 is controlled by the imaging system 100, which may trigger or invoke in the injector 114 to administer the contrast material. A contrast material(s) can alternatively be manually administered by a clinician or the like. Where the contrast material(s) is manually administered, the injector 114 can be omitted.

A reconstructor 116 reconstructs the projection data, generating volumetric image data. For perfusion imaging, this includes reconstructing a time series of contrast enhanced volumetric (3D) image data (or 4D data set) indicative of perfusion through scanned tissue of interest. A general-purpose computer serves as an operator console 118. Software resident on the console 118 allows the operator to interact with the scanner 100, e.g., to select a perfusion imaging protocol.

A processing system 126 processes 4D data sets generated by the imaging system 100 and/or other imaging system. In the illustrated embodiment, the processing system 126 obtains the 4D data set from the imaging system 100. In another instance, the processing system 126 obtains the 4D data set from a storage medium, for example, portable memory, a server, a database, a radiology information system (RIS), hospital information system (HIS), an electronic medical record (EMR), picture archive and communication system (PACS), and/or other data repository.

As described in greater detail below, the processing system 126 is configured to separate spatially entangled heterogeneous tissue components (classes) of scanned tissue into at least two different components, which allows for generating two or more different sets of perfusion maps for the same spatial region (voxel) of tissue, including an individual map for each of the tissue components. Examples of such tissue include, but are not limited to, normal tissue, tumoral tissue, liver tissue, lung tissue, a tissue region which includes a network or a mesh of small blood vessels passing through an organ parenchyma, and/or a mesh-like structure of lung tissue and air pockets between small segments of the tissue mesh.

The processing system 126 can be implemented via one or more processors executing one or more computer readable instructions embedded, encoded, etc. on computer readable storage medium such as physical memory and/or other non-transitory medium. Additionally or alternatively, at least one of the computer readable instructions can be carried by a carrier wave, signal, and/or other transitory medium.

Figure 2:
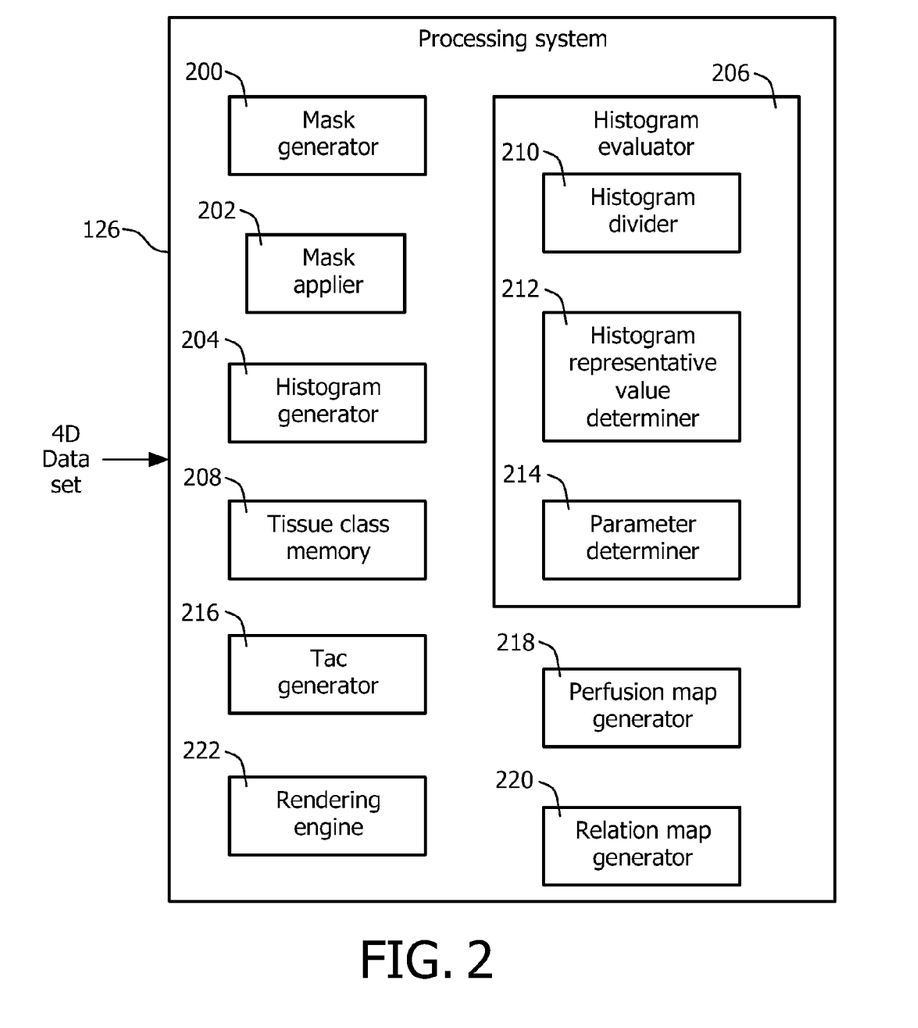
FIG. 2 schematically illustrates an example of the processing system of FIG. 1.

FIG. 2 schematically illustrates an example of the processing system 126. As shown, the processing system 126 receives as input the 4D data set.

Figure 3:
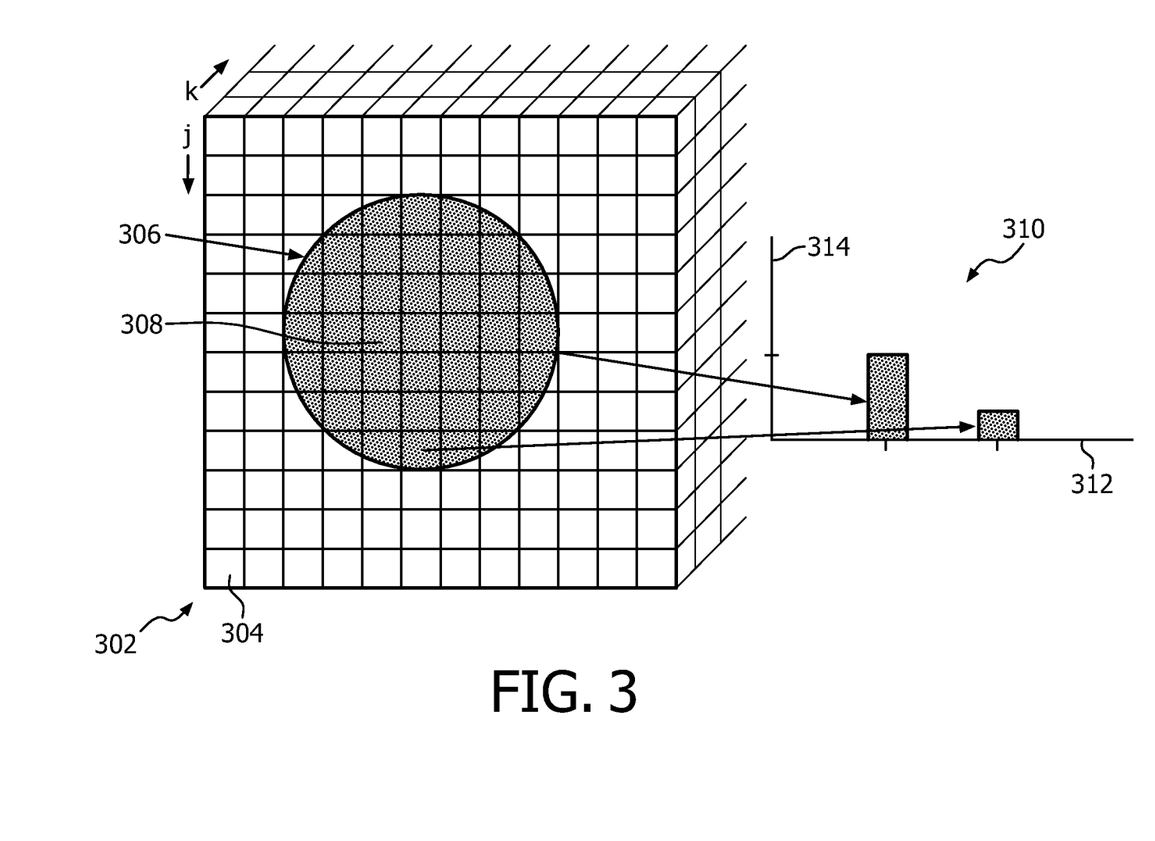
FIG. 3 illustrates a portion of volumetric image, a weighted mask, and a weighted histogram.

A mask generator 200 generates a mask of weights to weight values of voxels surrounding a voxel (or region of voxels) of interest currently being analyzed, and a mask applier 202 applies the mask to the voxel being analyzed. FIG. 3 shows a volume 302 of voxels 304 with a 3D Gaussian mask 306 applied thereto. The mask 306 has a defined sigma value (or width) and a defined cut-off in a certain radius distance from a voxel 308. Portions of voxels adjacent to the voxel 308 are weighted with a value close to one (1), and the value of the weights falls off with a distance of a voxel from the voxel 308. Other weighting functions (e.g., binary, linear, exponential, stepped, etc.) are also contemplated herein.

With reference to FIGS. 2 and 3, a histogram generator 204 generates a weighted histogram 310 for one or more of the voxels 304 and one or more time frames, e.g., each or a subset of the voxels 304 and/or the time frames based on the mask 306. In the example histogram 310, an x-axis 312 represents a value indicative of the image information (e.g., Hounsfield units in a CT image) and a y-axis 314 represents a value indicative a number of voxels for each HU value, after multiplying a contribution of each voxel 304 by a corresponding weight from the mask 306. For clarity and sake of brevity, FIG. 3 shows weighted contributions of only two of the voxels 304 and one time frame.

With the mask 306, if a voxel 304 is relatively far from the voxel 308 of interest, then the contribution of the voxel to the histogram in the y-axis 314 will be proportionally reduced, but its contribution to the x-axis 312 is not changed. In this way, a shape of the histogram 310 corresponding to a certain spatial position will not be very sensitive to any tissue miss-alignment between the successive time frames of the scan caused by motion and/or otherwise. In addition, the weighting pattern, which is decreased gradually out of the central voxel, will contribute to less-patchy perfusion maps. Generally, a histogram represents weighted image information surrounding an analyzed voxel.

By way of a more specific example, a non-limiting suitable 3D Gaussian mask 306 can be defined as $W_0(i,j,k) = \exp(-(i^2 \cdot r_x^2 + j^2 \cdot r_y^2 + k^2 \cdot r_z^2)/2/\xi^2)$, where $[r_x, r_y, r_z]$ are the directional mm/pixel scaling in the image volume, $[i,j,k]$ are the indexes (around the voxel of interest $[0,0,0]$) for which $W_0$ is above a determined threshold. A normalized weight mask W can be derived to satisfy $\Sigma\, W = 1$. The Gaussian width $\xi$ (in mm) determines the histogram 'clustering length'. The histogram bin partition in the relevant Hounsfield unit (HU) range is pre-defined. The weighted histogram is constructed in a process in which each voxel which is covered by the mask (in the vicinity of the voxel of interest) adds the corresponding mask weight to the height of the histogram bin which comprises the image voxel HU value. In this way, the weighting pattern, which is decreased gradually out of the central voxel, will contribute to smooth and less-patchy perfusion maps.

With respect to FIG. 2, a histogram evaluator 206 evaluates the weighted histograms and determines a representative value for each tissue component. In this example, the number of tissue components is pre-defined and stored in tissue class memory 208. In another instance, the number of tissue components is identified via a signal indicative of an user input identifying a desired number of tissue components, automatically determined based on 4D data set (e.g., based on the tissue scanned, the imaging protocol), etc. For sake of brevity and clarity, the following will describe an example in which the number of tissue components is two (2).

Figure 4:
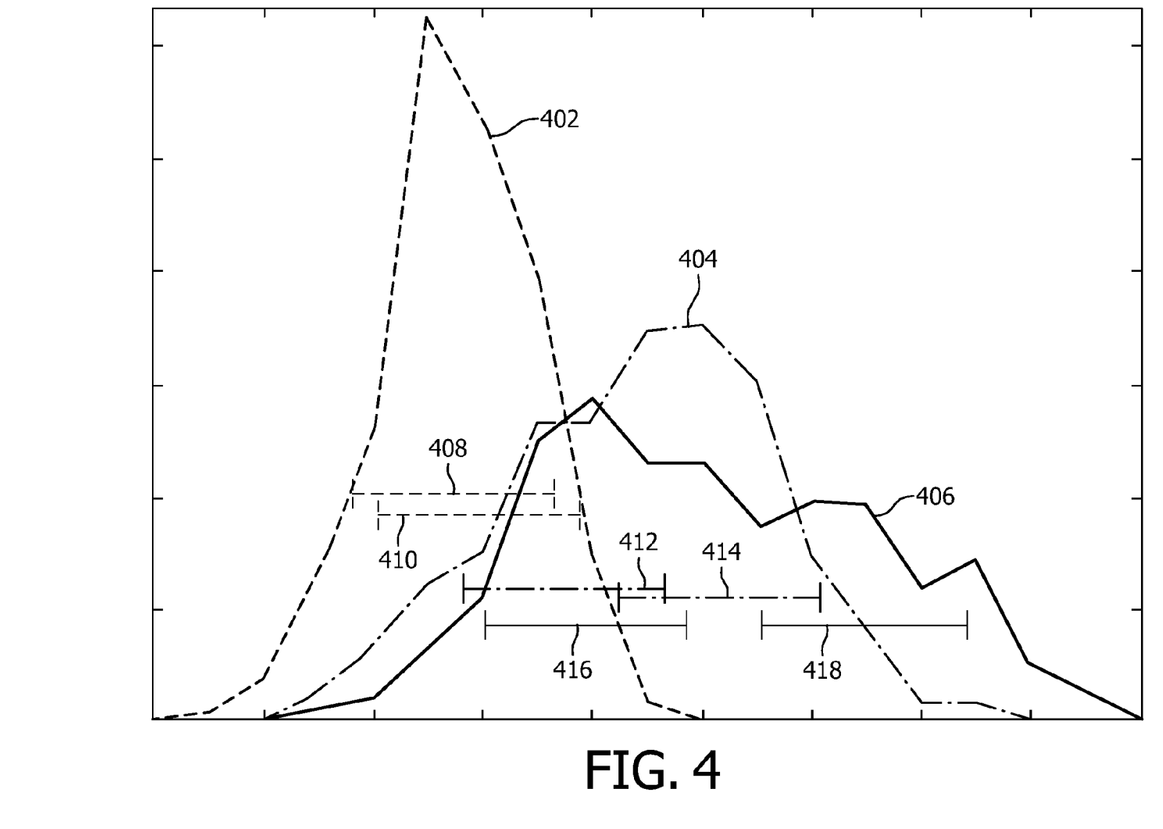
FIG. 4 illustrates example weighted histograms for a voxel for different volumes of the time series and tissue component ranges therein.

FIG. 4 shows three example histograms 402, 404, and 406 respectively representative of a same voxel for three different time frames. With reference to FIGS. 2 and 4, the histogram evaluator 206 includes a histogram divider 210 that divides each histogram into a number of sections or ranges equal to the number of components. As shown, the histogram 402 is divided into sections 408 and 410, which have equal widths and higher overlap (>50% overlap), the histogram 404 is divided into sections 412 and 414, which have equal widths and lower overlap (<50% overlap), and the histogram 406 is divided into sections 416 and 418, which have equal widths and no overlap, including a gap.

In another instance, at least two of the ranges have different widths. The histogram evaluator 206 further includes a histogram representative value determiner 212 that determines a representative value for each of the sections 408-418. In this example, the histogram representative value determiner 212 determines a representative value by determining a momentum (e.g., first, second, or higher order) around each section of the sections 408-418. The widths can further define weights for calculating the momentum. Other approaches are also contemplated herein.

Figure 5:
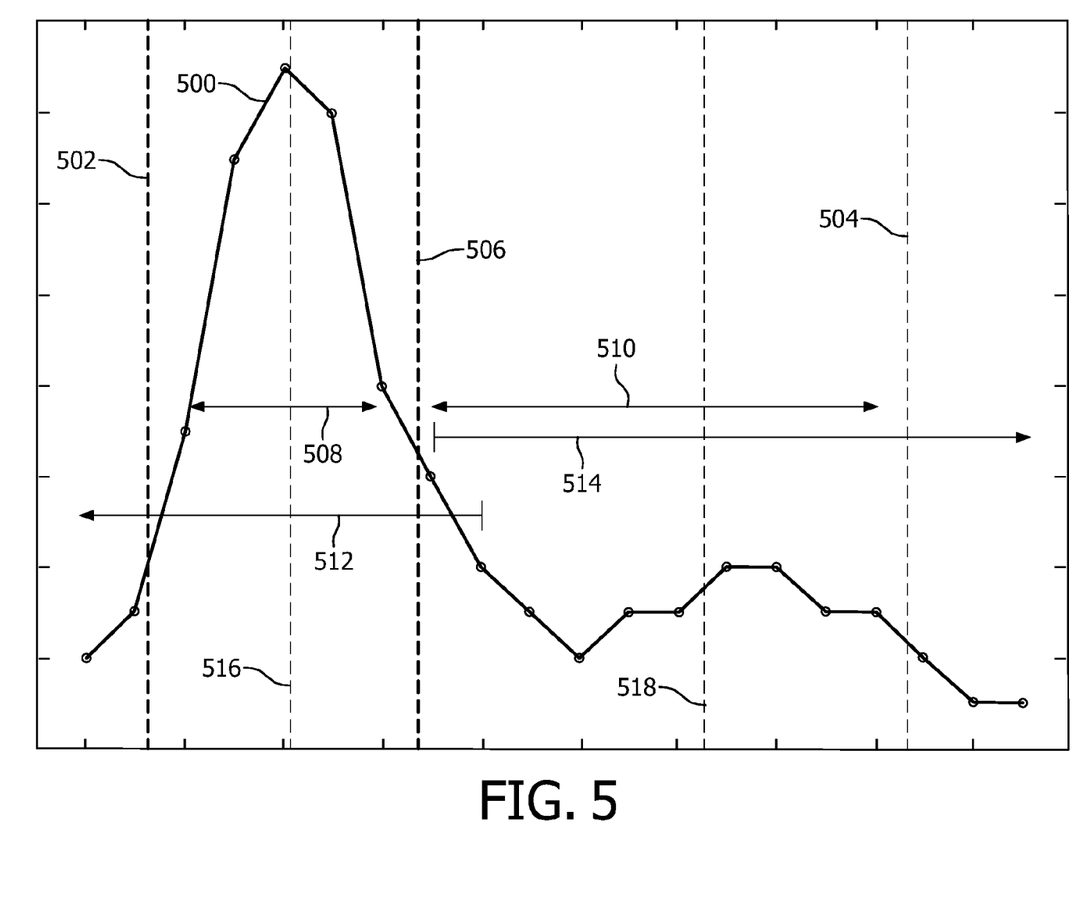
FIG. 5 illustrates an example of a weighted histogram for a voxel for a volume of the time series and tissue component ranges therein.

FIG. 5 illustrates another example. For this example, a single histogram 500 analysis for two tissue components is described.

With reference to FIGS. 2 and 5, the histogram divider 210 determines a lower threshold 502 as a HU value above histogram data points from a lower HU range, which, in the illustrated embodiment, represents an area below 5% (or other percent) of the total area, and a higher threshold 504 as a HU value below the histogram data points from a higher HU range, which, in the illustrated embodiment, has the area below 5% (or other percent) of the total area. The histogram representative value determiner 212 calculates a "center of gravity" 506 of the total histogram 500, for example, as ($\Sigma$ $x_i \cdot y_i$)/($\Sigma$ $y_i$), where $y_i$ are the histogram bin heights and $x_i$ are the HU values of the bin positions. The histogram representative value determiner 212 calculates a HU range 508 of the histogram 500 between 502 and 506, and calculates a HU range 510 of the histogram 500 between 506 and 504.

If a length of 508 is less than a predetermined model parameter, then 508 is extended to a right side by a difference between the model parameter and the length (or until the right margin of the histogram, if it is narrower). In the illustrated example, the length of 508 is less than the model parameter and thus extended to the right. The length 508 is also extended to the lower HU margin of the histogram, creating the range 512. If a length of 510 is less than the model parameter, then 510 is extended to a left side by a difference between the model parameter and the length (or until the left margin of the histogram, if it is narrower). In the illustrated example, this is not required since the length of 510 is greater than the model parameter. The length 510 is also extended to the higher HU margin 504 of the histogram 500, creating the range 514.

The histogram representative value determiner 212 calculates a "center of gravity" 516 for the range 512. For this, the data points which are covered both by 512 and 514 (two points in the example) contribute half of their values to the "center of gravity" calculation of the 512 range, determining 516. The histogram representative value determiner 212 calculates a "center of gravity" 518 for the range 514. For this, the data points which are covered both by 512 and 514 (two points in the example) contribute half of their values to the "center of gravity" calculation of the 514 range, determining 518. The HU values 516 and 518 are the representative distribution values of the two tissue components in this position and time frame.

With respect of FIG. 2, a parameter determiner 214 determines one or more parameters from the histograms. For example, in one instance, the optional parameter determiner 214 determines relations between the relative-volumes of the different components based on the histograms. The relative-volume of a tissue class can be determined as the weighted area in a relevant section of a histogram. The parameter relation can be determined as a ratio, for example, between the relative-volume of the tissue components (or other similar function). Other parameter relations are also contemplated herein.

By way of further example, in connection with FIGS. 2 and 5, the parameter determiner 214 calculates a total area under the histogram values of range 512 divided by the total histogram area and calculates a total area under the histogram values of range 514 divided by the total histogram area. For both cases, the data points which are covered both by 512 and 514 (two points in the example) contribute half of their values to the sum of the values in 512 and 514. In the illustrated example, the result for the first relative volume is 66.3% and the result for the second relative volume is 33.7%.

Figure 6:
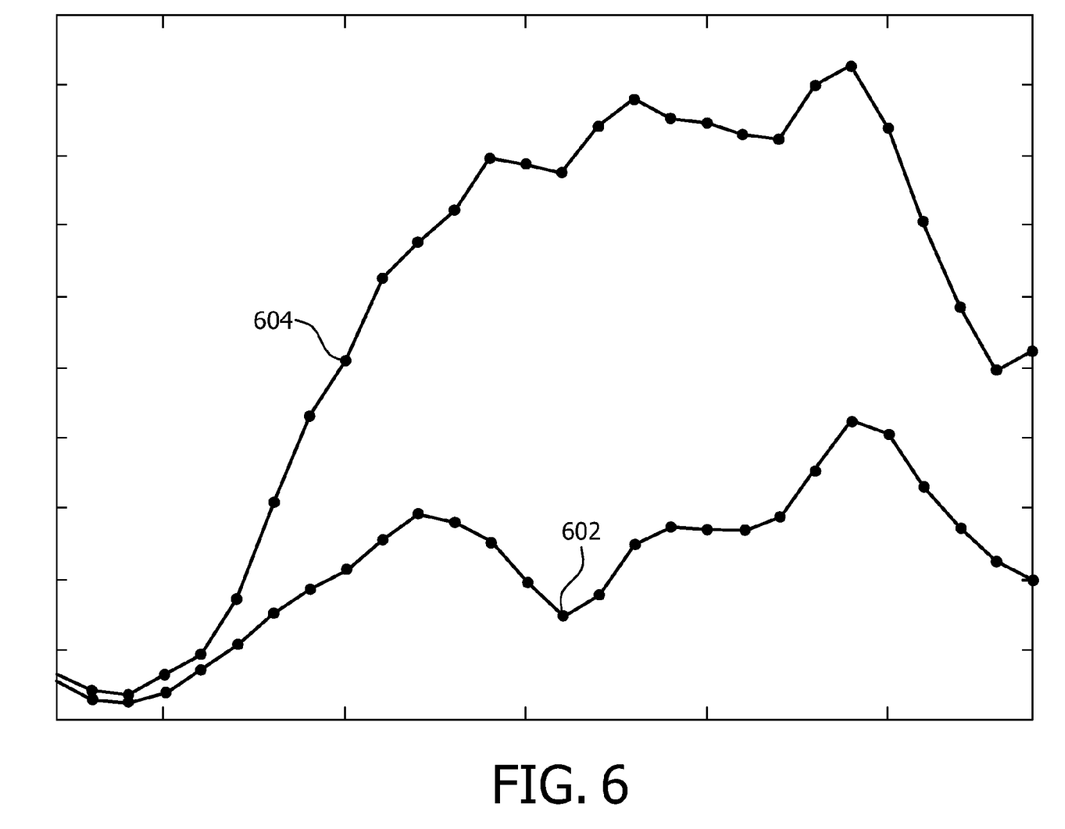
FIG. 6 illustrates example multiple TACs generated for different tissue components from a histogram.

With respect of FIG. 2, a time activity curve (TAC) generator 216 generates time activity curves (TACs) for the voxels 304 based on the sections of the histograms. Continuing with the above example with two tissue classes, two TAC points are generated for each histogram, one TAC point for each section. FIG. 6 shows an example of two TACs 602 and 604 for sets of two sections of each histogram along the measured time frames. To determine the two TACs 602 and 604, the TAC generator 216 employs an algorithm that finds which of the data points (of a specific time frame) belongs to each of the tissue classes. For this, a model of the blood flow pattern in the relevant presumed tissue can be used to facilitate determining this information.

Figure 7:
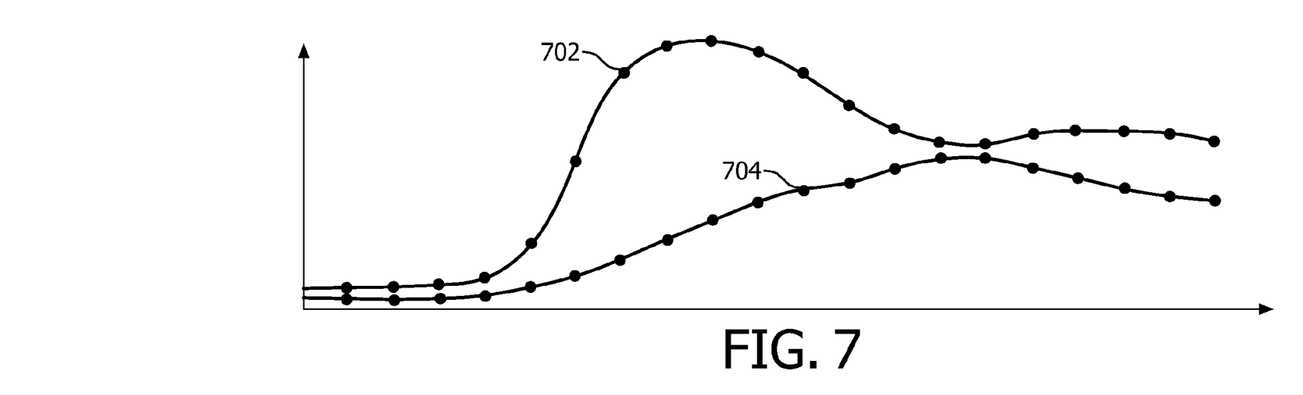
FIG. 7 illustrates a first model for determining the multiple TACs of FIG. 6.
Figure 8:
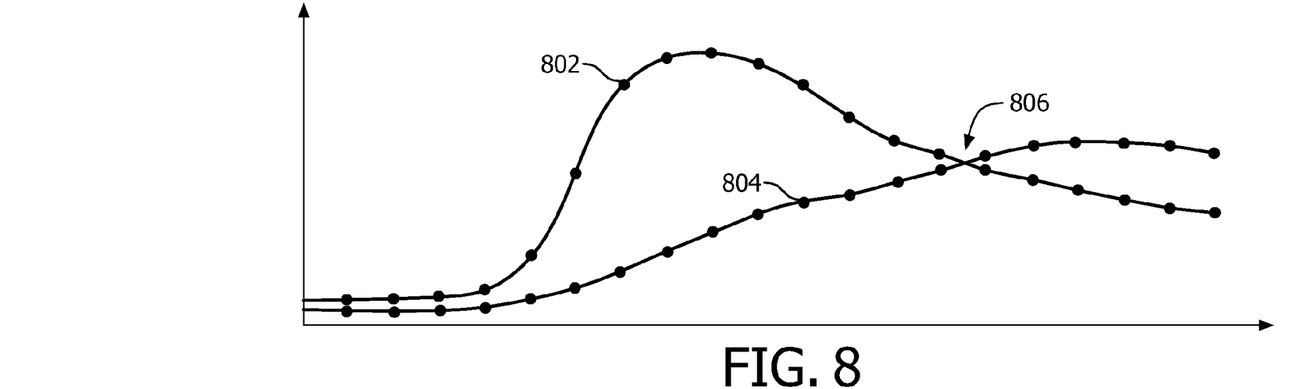
FIG. 8 illustrates a second different model for determining the multiple TACs of FIG. 6.

FIGS. 7 and 8 show examples of such a model. In FIG. 7, the model assumes (e.g., based on an a priori knowledge about the organ) that a single circulatory flow is relevant (e.g. an arterial flow only). As such, an example division pattern is one tissue class (profile 702) that mainly contains blood vessels and has a higher contrast enhancement and a second tissue class (profile 704) such as an organ parenchyma that has a lower contrast enhancement. In FIG. 8, two different circulatory flows are assumed, a first flow in a first tissue class (profile 802) and a second flow in a second tissue class (profile 804). In this example, the two profiles 802 and 804 cross at 806.

Figure 9:
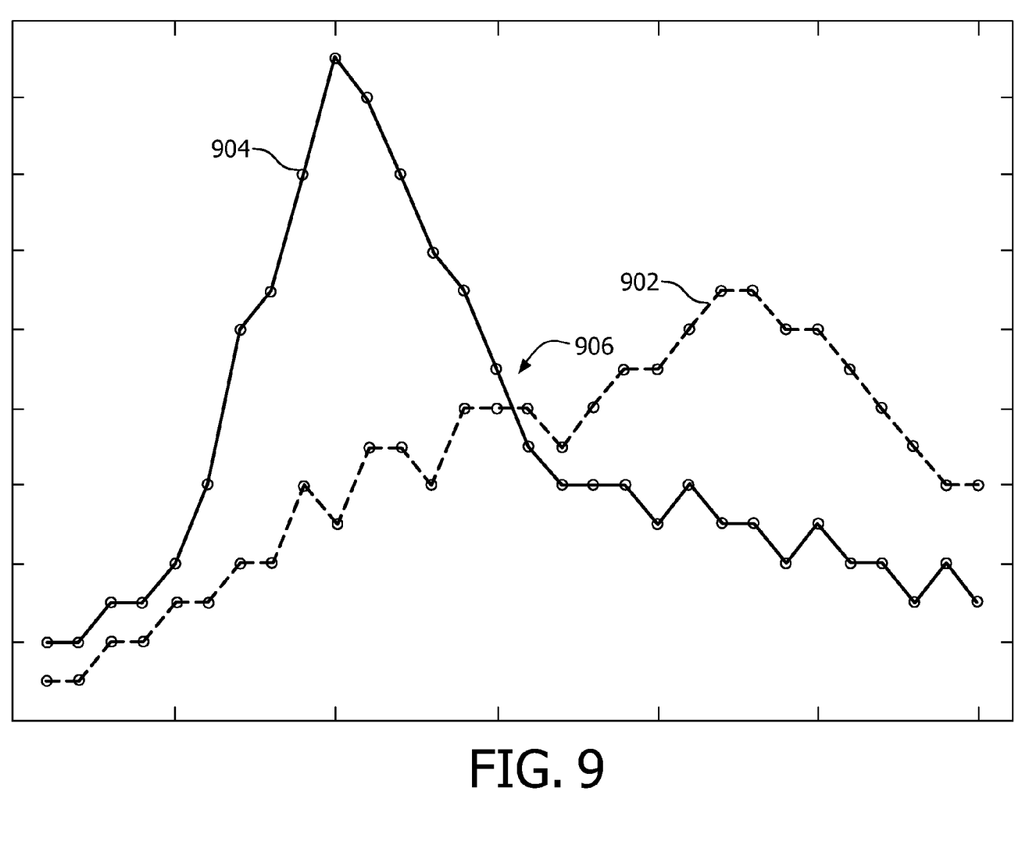
FIG. 9 illustrates another example of multiple TACs generated for different tissue components from a histogram.

With reference to FIGS. 5 and 9, another example in which points in a pair of TAC values belong to each of the two tissue classes. Following FIG. 5, there are two data points for each time frame. The TAC generator 216 first determines which of the two data points in each time frame belongs to the first tissue component and which to the second tissue component. Generally, the type of perfusion patterns in the scanned organ can be predicted. For example, in the lung tissues there can be the earlier pulmonary circulation and the later arterial circulation, in the liver there can be the earlier arterial circulation and the later hepatic portal circulation, in many other organs, only arterial circulation is possible, etc.

In a simple case, where only a single circulation is predicted, the model can select in each time frame a lowest data point in a pair for a first tissue component, and a highest data point in a pair for the second tissue component, as shown in FIG. 6. This will result in the first TAC 602 with relatively low perfusion and the second TAC 604 with relatively high perfusion. In a more complicated case, where two different circulations are predicted, other model conditions can be determined. An example for such a model is related to the data points in FIG. 9. With this model, data points are grouped in such a way that a sum of the two absolute values of the two second derivatives is minimal. In a discrete form, the second derivative (for an arbitrary vector z) is: $z(i)+z(i-2)-2*z(i-1)$.

More particularly, in a data set with N time frames and two initial data sets $y1(1:N)$ of the lower values (of each pair) and $y2(1:N)$ of the higher values (of each pair), the values in two TACs $c1(1:N)$ and $c2(1:N)$ are arranged in such a way that they will fit the defined model (in this example, the minimal second derivatives). In the simple scheme below, the first two time frames are determined in a trivial way, and the other time frames are determined serially according to the conditions:

```
Set: c1(1)=y1(1); c2(1)=y2(1); c1(2)=y1(2); c2(2)=y2(2);
for i=3:N
    g1=abs(y1(i)+c1(i-2)-2*c1(i-1))+abs(y2(i)+c2(i-2)-2*c2(i-1));
    g2=abs(y2(i)+c1(i-2)-2*c1(i-1))+abs(y1(i)+c2(i-2)-2*c2(i-1));
    if g1>g2
        c1(i)=y2(i);
        c2(i)=y1(i);
    else
        c1(i)=y1(i);
        c2(i)=y2(i);
    end
end
```

Two calculated TACs 902 and 904 are shown in FIG. 9 and represent correctly the arterial circulation and the portal circulation in a simulated liver scan data. The correct identification of a crossing region 906 of the two TACs is a result of the model condition. It is also possible to add conditions for robustness against noise such as data smoothing and checking curve derivative on different scales.

Figure 10:
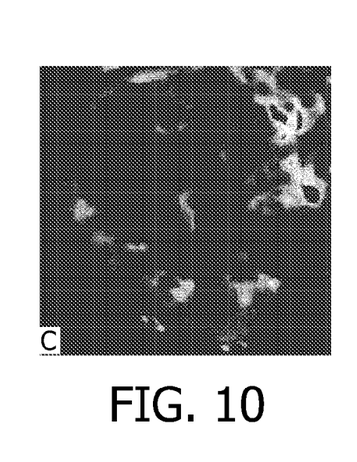
FIG. 10 illustrates a perfusion map for one of a plurality of separated entangled tissue components.
Figure 11:
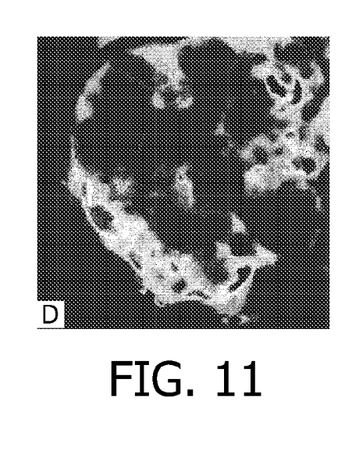
FIG. 11 illustrates a perfusion map for a second of the plurality of separated entangled tissue components.
Figure 12:
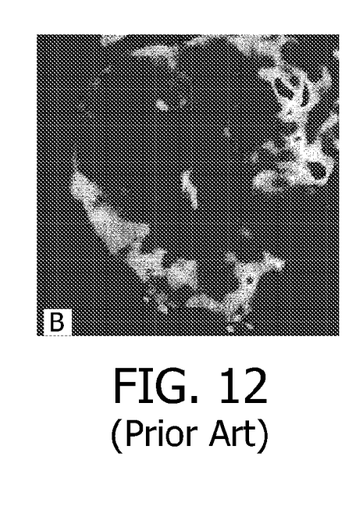
FIG. 12 illustrates a prior art perfusion map, where the tissue components are not separated, after smoothing the image data of all time frames
Figure 13:
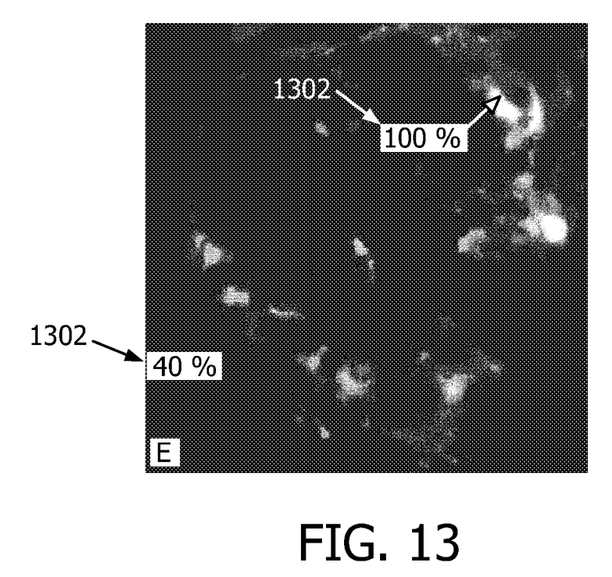
FIG. 13 illustrates a relation map for one of a plurality of separated entangled tissue components.
Figure 14:
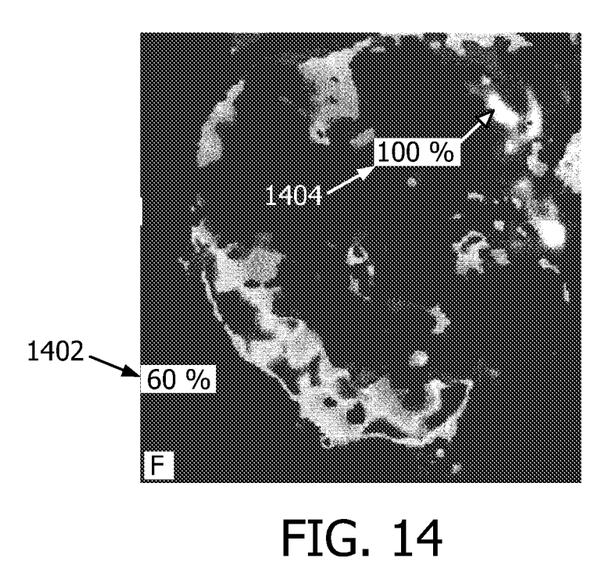
FIG. 14 illustrates a relation map for another of the plurality of separated entangled tissue components.

Returning to FIG. 2, a perfusion map generator 218 generates one or more perfusion maps based on the TACs. The volumetric perfusion maps can be calculated using a standard or other technique and include maps for blood flow, blood volume, mean transit time, time of arrival, permeability, time to peak, peak intensity, maximal gradient, and/or other parameters. FIGS. 10 and 11 respectively show a first perfusion map of a first tissue-component with a lower perfusion and a second perfusion map of a second tissue-component with a higher perfusion. FIG. 12 shows a prior art perfusion map, where the tissue components are not separated, after smoothing the image data of all time frames.

Where the parameter determiner 214 determines relations between the relative-volumes of the different tissues classes based on the histograms, a relation map generator 220 generates a parameter relation map between the tissue components. FIGS. 13 and 14 show examples of such a map, in grayscale. Optionally, color can additionally or alternatively be used. For FIGS. 13 and 14, if the two tissue classes are likely identical (i.e. the voxel contains a single tissue component), then the voxel is represented via a predetermined gray level. A grayscale (or a color scale) is used for voxels including at least two tissue classes.

In the illustrated example, in response to hovering a curser over a voxel in FIG. 13 or 14, a relative contribution of a tissue component in the image is presented, as shown at 1302, 1304, 1402 and 1404 in FIGS. 13 and 14. By way of example, in the illustrated embodiment, a first tissue component is shown at 1302 to be 40% of the tissue at that voxel and a second tissue component is shown at 1402 to be 60% of the tissue at that voxel. A same single tissue component (e.g., the first component, the second component or another component) is shown at 1304 and 1404 to be 100% of the tissue at that voxel.

A rendering engine 222 visually presents one or more of the perfusion maps (FIGS. 10 and 11) and/or relation maps (FIGS. 13 and 14).

Figure 15:
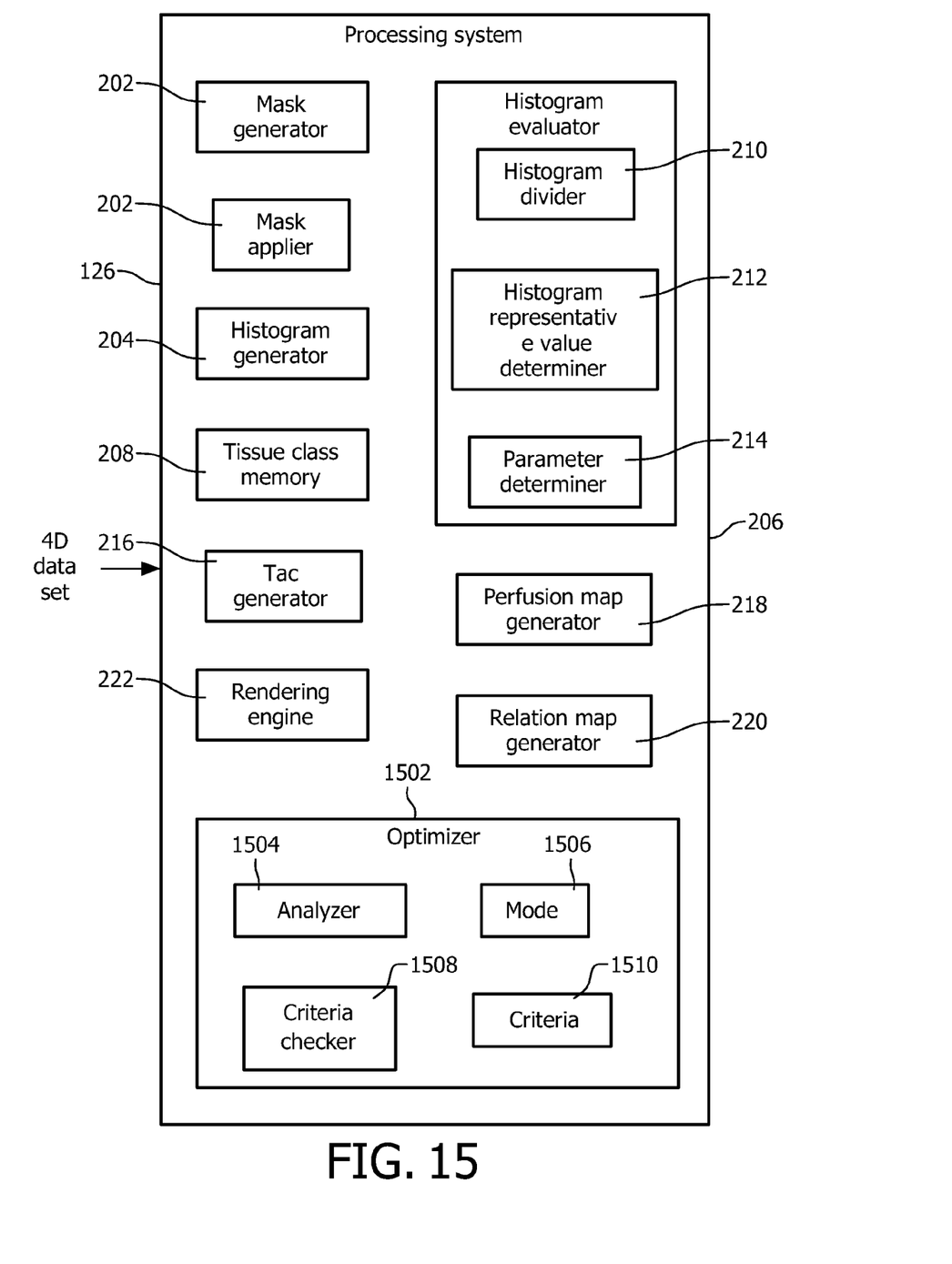
FIG. 15 schematically illustrates a variation of the processing system which includes an optimizer.

FIG. 15 shows a variation of FIG. 2 in which the processing system 126 further includes an optimizer 1502. The optimizer 1502 includes an analyzer 1504 that compares the time series of the tissue parameter relation values with a pre-defined model 1506, which defines a likelihood of the parameter relation pattern between the multiple tissue classes. A criteria checker 1508 checks the result of the comparison against pre-determined criteria 1510.

If the result satisfies the pre-determined criteria 1510, the generated TACs are utilized to generate the parameter maps as discussed above. If not, the histogram divider 210 is invoked to employ a different set of ranges for each histogram for a subsequent TAC generation iteration. Such iterations can be repeated until the optimization criteria are met, pre-defined limits of iteration numbers is reached, a change between iteration results is sufficiently small, a predetermined processing time elapses, etc.

By way of a more detailed non-limiting example, after determining the TACs, each point in a TAC has its calculated relative volume (the relation parameter). These values set a type of mutual relation between the two tissue classes. The model 1506 determines how to use these relations for the optimization. An example model determines that the relative volume of a tissue class should be ideally maintained along all time frames (for each specific position).

The deviation from the pure model can be calculated as follows to create a cost function: For a given position (voxel) having sets of TAC data points, calculate a mean relative volume of each tissue class (the mean is along the time frame axis), calculate a sum of squares of distances between the calculated relative volumes to the mean value, and define the tissue relation cost function as a sum of the multiple sum of squares of distances.

For the optimization, multiple cost functions are determined, one for each of the models. A cost function determines the weight in the optimization of the deviation of the actual results from the pre-defined model. An example for an optimization criterion is that the sum of all three cost functions should be minimized. The optimization process (the data modification) can be done by shifting the values of center of gravity e.g., 506 in FIG. 5, in each time frame to the left or right of the histogram and calculating again the whole process.

An example first cost function is the sum of squares of the distances between the new set of center of gravities to the original set of center of gravities (possibly multiplied by a pre-defined constant weight). An example second cost function is the sum of the second derivatives of the two TACs (possibly multiplied by a pre-defined constant weight). An example third cost function is the tissue relation cost function described above (possibly multiplied by a pre-defined constant weight).

Another optimization step (or an intermediate step) can be to change the TACs definition (the deviation between the representative tissue class values in block 5) without changing the values of the center of gravity, if this contributes to the minimization of the total cost function. The direction and magnitude of changing the center of gravity 506 during the optimization is set according to the deviation of the relation parameter (for each time frame) from the model.

For example, if for a certain position and a certain time frame the relative volume of the first tissue class is larger than the calculated mean relative volume of the first TAC, and the relative volume of the second tissue class is smaller than the calculated mean relative volume of the second TAC, then during the optimization 506 should be shifted to the left of the histogram (with a pre-defined shift magnitude) to potentially reduce the volume of the first tissue class and to increase the relative volume of the second tissue class. In this way, the optimization can rapidly converge to a "best" solution.

Figure 16:
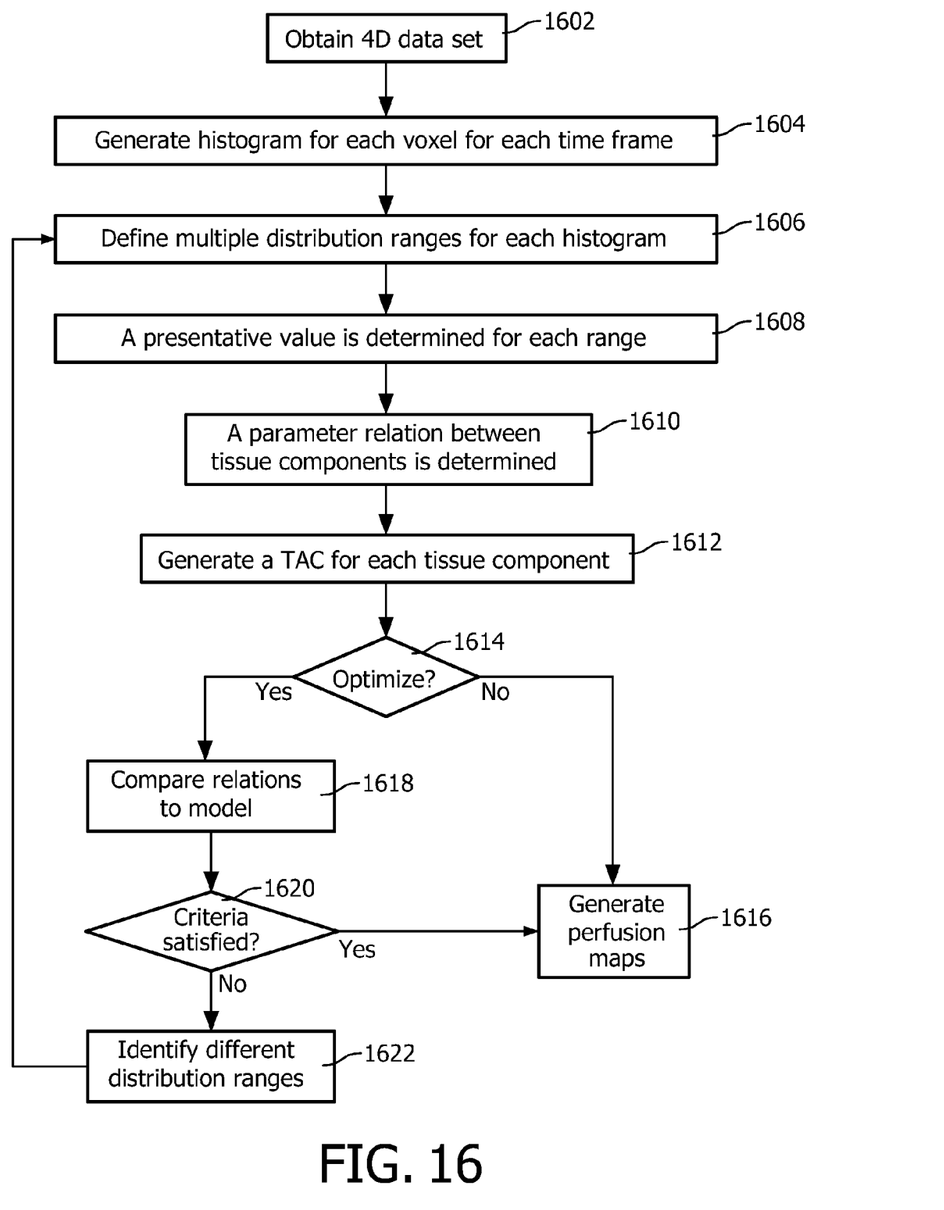
FIG. 16 schematically illustrates a method for separating spatially entangled heterogeneous tissue components.

FIG. 16 illustrates a method for separating entangled heterogeneous tissue components and generating individual TACs for the individual tissue components.

It is to be appreciated that the ordering of the acts is not limiting. As such, other orderings are contemplated herein. In addition, one or more acts may be omitted and/or one or more additional acts may be included.

At 1602, a 4D data set of a contrast enhanced dynamic scan is obtained.

At 1604, a histogram is generated for each spatial position (i.e., voxel or region) in the 4D data set to be evaluated for each time frame to be evaluated.

At 1606, for each histogram, multiple distribution ranges are defined for multiple tissue components, one range for each tissue component.

At 1608, a representative value for each range is determined.

At 1610, a parameter relation between the multiple tissue components is determined based on the histograms and ranges.

At 1612, a TAC is generated for each tissue component based on the representative values of each time frame and a likelihood of TAC patterns of the multiple tissue components.

At 1614, it is determined whether a TAC optimization is to be performed.

If not, then at 1616, a perfusion map for each class is created based on the corresponding TAC and at least one of the perfusion maps is visually presented and, optionally, relation maps are created and visually presented.

If so, then at 1618 the parameter relations are compared to a model that defines a likelihood of the parameter relation pattern between the multiple tissue components.

At 1620, the result is checked to see whether is satisfies predetermined criteria.

If so, then act 1616 is performed.

If not, then at 1622 a set of different ranges are identified and act 1606 is repeated.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
   obtaining a 4D data set in electronic format, wherein the 4D data set includes a plurality of 3D volumes of voxels of contrast enhanced perfusion imaging data for two or more time frames, and the 3D volumes include data representative of at least two different tissue components in a same region of interest in at least one of the time frames;
   generating a different time activity curve point for each of the different tissue components for each voxel being evaluated for each time frame being evaluated; and
   generating a signal indicative of a different parameter map for each of the different tissue components based at least on the time activity curves.

2. The method of claim 1, further comprising:
   applying a mask to a sub-portion of a 3D volume about a voxel of interest; and
   generating a histogram for the voxel based on voxels within the mask,
   wherein a time activity curve corresponding to the voxel is generated based on the histogram.

3. The method of claim 2, wherein the mask applies different weights to values of different voxels based on a distance of a voxel to the voxel of interest.

4. The method of claim 2, further comprising:
   dividing the histogram into at least two different ranges, each range corresponding to a different tissue component;
   calculating a representative value for each of the at least two ranges; and
   determining a time activity curve point for each of the ranges, thereby determining a time activity curve for each of the different tissue components.

5. The method of claim 4, further comprising:
   determining the time activity curve based on a predetermined model that defines a likelihood of each of a plurality of different time activity curve patterns.

6. The method of claim 4, further comprising:
   determining a parameter relation between the different tissue components based on the histogram and the ranges; and
   generating a second signal indicative of a different relation map for each of the different tissue components based the parameter relation.

7. The method of claim 6, further comprising:
   comparing the parameter relation to pre-determined data representing a likelihood of parameter relations between the different components;
   checking a result of the comparison with pre-defined criteria; and
   visually presenting at least the parameter maps in response to the results satisfying the pre-defined criteria.

8. The method of claim 7, further comprising:
   in response to the results not satisfying the pre-defined criteria:

modifying the at least two ranges, generating at least two modified ranges;
dividing the histogram into the at least two modified ranges;
calculating a subsequent representative value for each of the at least two modified ranges; and
determining a subsequent time activity curve point for each of the modified ranges, thereby determining a subsequent time activity curve for each of the different tissue components.

9. The method of claim 8, further comprising:
repeating the acts of modifying the ranges, dividing the histogram hosed on the modified ranges, calculating the subsequent representative value, and determining the subsequent time activity curve until stopping criteria is reached.

10. The method of claim 9, wherein the stopping criteria includes at least one of: a pre-defined number of iterations is reached, a difference in the results between sequential iterations is below a predetermined threshold, or a predetermined amount of time elapses.

11. A processing system, comprising:
a histogram generator configured to generate a histogram for each voxel being evaluated in a plurality of 3D volumes of voxels of contrast enhanced perfusion imaging data for two or more time frames, wherein the 3D volumes include data representative of at least two different tissue components in a same region of interest in at least one of the time frames;
a time activity curve generator configured to generate a different time activity curve point for each of the different tissue components for each voxel being evaluated for each time frame being evaluated; and
perfusion map generator configured to generate a signal indicative of a different parameter map for each of the different tissue components based at least on the time activity curves.

12. The processing system of claim 11, further comprising: a mask applier configured to apply a mask to a sub-portion of a 3D volume about a voxel of interest, wherein the histogram generator generates a corresponding histogram for the voxel based on voxels within the mask, and a time activity curve corresponding to the voxel is generated based on the histogram.

13. The processing system of claim 12, wherein the mask applies different weights to values of different voxels based on a distance of a voxel to the voxel of interest, wherein the weights are based on at least one of a Gaussian, binary, linear, exponential or stepped distribution.

14. The processing system of claim 12, further comprising:
a histogram evaluator configured to divide each of the histograms into at least two different ranges, each range corresponding to a different tissue component, calculates a representative value for each of the at least two ranges, and
determines a time activity curve point for each of the ranges, thereby determining a time activity curve for each of the different tissue components.

15. The processing system of claim 14, wherein the time activity curve is determined based on a predetermined model that defines a likelihood of each of a plurality of different time activity curve patterns.

16. The processing system of claim 14, further comprising:
a parameter determiner configured to determine a parameter relation between the different tissue components based on the histogram and the ranges; and
a relation map generator configured to generate a different relation map for each of the different tissue components based the parameter relation.

17. The processing system of claim 16, further comprising:
an optimizer, including:
an analyzer configured to compare the parameter relation to pre-determined data representing a likelihood of parameter relations between the different; components; and
a criteria checker configured to check a result of the comparison with pre-defined criteria, and
a rendering engine configured to visually present at least the parameter maps in response to the results satisfying the pre-defined criteria.

18. The processing system of claim 17, wherein, in response to the results not satisfying the pre-defined criteria, the histogram evaluator divides the histogram into the at least two modified ranges, calculates a subsequent representative value for each of the at least two modified ranges, and determines a subsequent time activity curve point for each of the modified ranges, thereby determining a subsequent time activity curve for each of the different tissue components.

19. The processing system of claim 18, wherein the histogram evaluator repeats the acts of modifying the ranges, dividing the histogram based on the modified ranges, calculating the subsequent representative value, and determining the subsequent time activity curve until stopping criteria is reached.

20. A non-transitory computer readable storage medium encoded with one or more computer executable instructions, which, when executed by a processor of a computing system, causes the processor to:
obtain a 4D data set in electronic format, wherein the 4D data set includes a plurality of 3D volumes of voxels of contrast enhanced perfusion imaging data for two or more time frames, and the 3D volumes include data representative of at least two different tissue components in a same region of interest in at least one of the time frames;
generate a different time activity curve point for each of the different tissue components for each voxel being evaluated for each time frame being evaluated; and
generate a signal indicative of a different parameter map for each of the different tissue components based at least on the time activity curves.

* * * * *